(12) United States Patent
Weber

(10) Patent No.: US 7,189,213 B1
(45) Date of Patent: *Mar. 13, 2007

(54) ARM SUPPORT IN SLING

(75) Inventor: James J. Weber, Santa Barbara, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 589 days.

This patent is subject to a terminal disclaimer.

(21) Appl. No.: 10/718,058

(22) Filed: Nov. 21, 2003

(51) Int. Cl.
*A61F 5/00* (2006.01)
(52) U.S. Cl. .............................. 602/20; 602/4
(58) Field of Classification Search ............... 602/4–6, 602/12, 13, 15, 16, 20, 21, 60–62, 64, 77; 128/869, 878–881; 2/44, 45; 604/179; 606/54; 5/646–647, 640, 922
See application file for complete search history.

(56) References Cited

U.S. PATENT DOCUMENTS

| | | | |
|---|---|---|---|
| 3,638,334 A | 2/1972 | Malikowski | |
| 4,039,039 A | 8/1977 | Gottfried | |
| 4,683,601 A | 8/1987 | Lagin | |
| 4,841,961 A | 6/1989 | Burlage et al. | |
| 5,000,169 A | 3/1991 | Swicegood et al. | |
| 5,334,132 A * | 8/1994 | Burkhead | 602/4 |
| 5,358,470 A * | 10/1994 | Johnson | 602/20 |
| 5,383,844 A * | 1/1995 | Munoz et al. | 602/20 |
| 5,449,965 A | 9/1995 | Tsuru | |
| 5,566,682 A | 10/1996 | Yavitz | |
| 5,569,172 A * | 10/1996 | Padden et al. | 602/20 |
| 5,738,640 A | 4/1998 | Carlson-Orsi | |
| 6,009,873 A | 1/2000 | Neviaser | |
| D445,506 S | 7/2001 | Vinson et al. | |
| 6,438,779 B1 | 8/2002 | Brown | |
| 6,659,971 B2 * | 12/2003 | Gaylord | 602/4 |
| 6,949,077 B2 * | 9/2005 | Froom | 602/21 |
| 6,979,303 B2 * | 12/2005 | Jestrabek-Hart | 602/4 |
| 2004/0215119 A1 * | 10/2004 | Avon | 602/4 |

* cited by examiner

*Primary Examiner*—Patricia Bianco
*Assistant Examiner*—Kiandra C Lewis
(74) *Attorney, Agent, or Firm*—William W. Haefliger

(57) ABSTRACT

An arm supporting pillow in sling apparatus, comprising in combination a flexible sling, with a strap to be supported by a user's shoulder area, an insert pillow received in the sling, to be retrievable from the sling, the sling and pillow dimensioned to receive a user's forearm alongside the pillow, in the sling.

14 Claims, 5 Drawing Sheets

ARM SUPPORT IN SLING

BACKGROUND OF THE INVENTION

This invention relates generally to human arm supports, and more particularly to comfortably supporting that forearm in an immobile position, spaced from the torso.

There is need for such arm supporting device, and particularly after surgery, and when a patient is bedridden. In particular, there is need for a simple, effective, arm support that is easily applied with minimum disturbance to the arm itself.

SUMMARY OF THE INVENTION

It is a major object of the invention to provide an improved arm support apparatus meeting the above need, and employing an arm supporting pillow. Basically the invention is embodied in a sling apparatus that comprises, in combination:

a) a flexible sling, with a strap to be supported by a user's shoulder area, b) an insert pillow received in the sling, and to be retrievable from the sling, c) the sling and pillow dimensioned to receive a user's forearm alongside the pillow, in the sling.

As will be seen, the pillow typically has a width between 2½ and 5 inches, to support the forearm at that distance from the human torso to which the sling is applied, the pillow extending forwardly, along side the forearm and held in that position by the sling. Also, the pillow preferably consists of foam material, and has a jacket covering the foam material, and may have releasable connection to the sling for positioning.

It is another object of the invention to provide a sling having forwardly extending panels which are foldable to be connectable together along upper extent of the sling, to close the sling over the user's forearm and pillow, and to allow upward opening of the sling to release the user's forearm and the pillow.

Yet another object is to provide a strap that extends above the user's body and has opposite ends respectively connected to the sling and to the pillow, and having length to extend about the user's body.

A further object is to provide a sling having a releasable drop panel which, when dropped, allows the user's forearm to dangle downwardly from and below the sling. A user's hand holder associated with the pillow is manipulable to release the hand and arm, to hang downwardly as described.

An added object is to provide a sling having a bottom panel which is adjustable in width to allow sling size adjustment. Such sling size adjustment easily accommodates to different size (width) arms to be retained against the side of the pillow by the sling, so that only one size pillow is needed, but multiple sizes are accommodated.

The novel sling and pillow apparatus therefore has many advantages as well as multiple modes of operation, all embodied within a single, effective, easily applied and removed apparatus, particularly as respects bedridden patients.

These and other objects and advantages of the invention, as well as the details of an illustrative embodiment, will be more fully understood from the following specification and drawings, in which:

DRAWING DESCRIPTION

DETAILED DESCRIPTION

Figure 1:
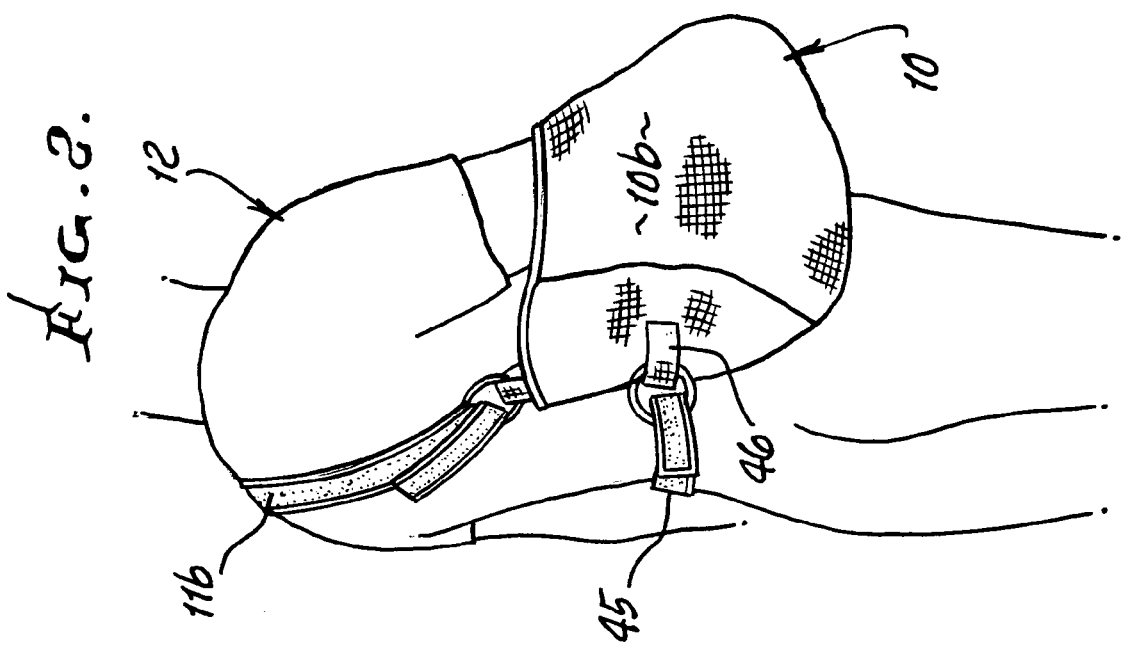
FIGS. 1 and 2 are frontal and rearward perspective views of preferred apparatus embodying the invention.

In the drawings, a flexible sling 10 has a strap 11 to be supported by a user's shoulder area 12*a*, so that the strap extends at 11*a* at the front of the user's body 12, and at 11*b* at the rear of the body.

Figure 7:
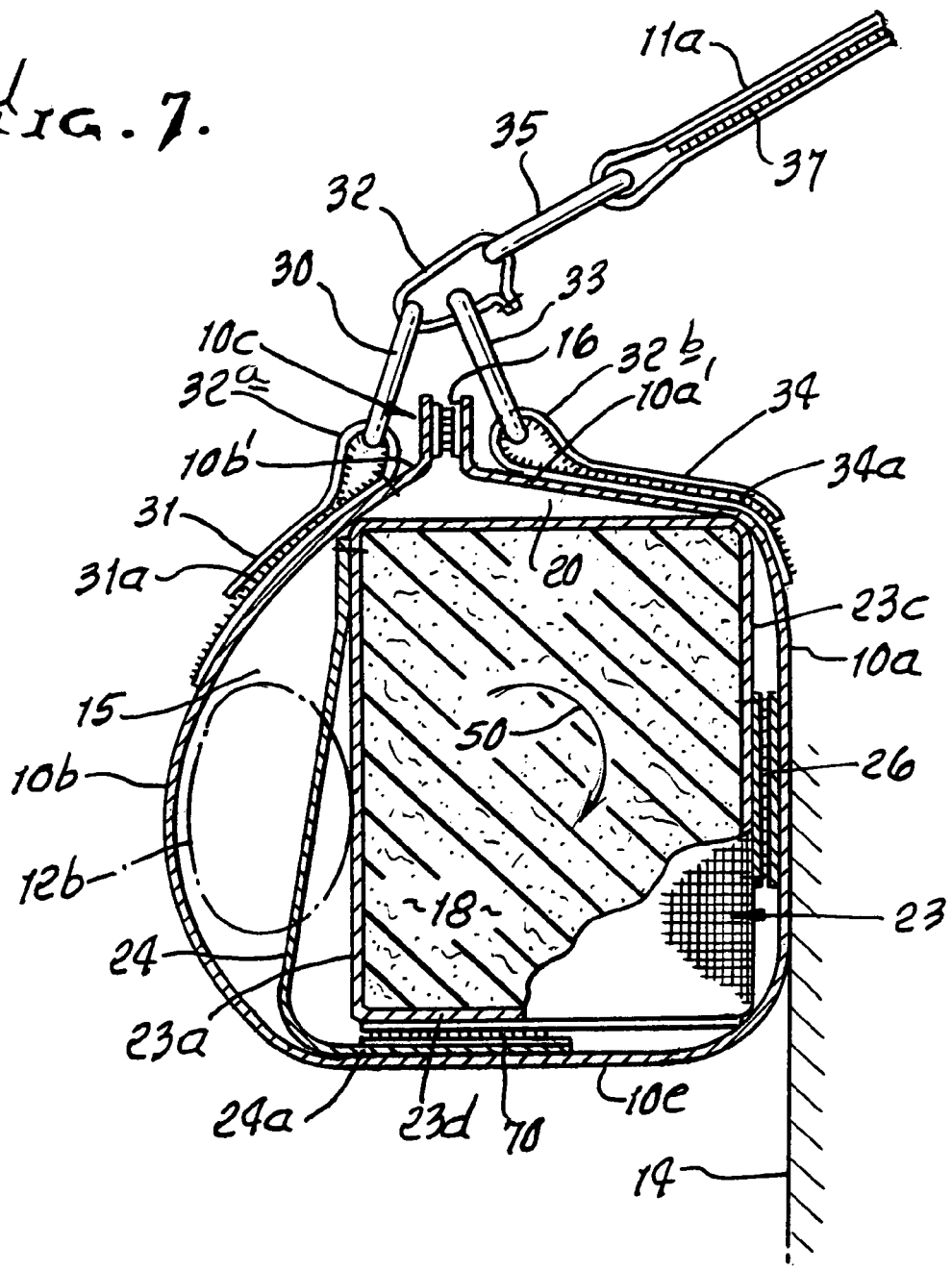
FIG. 7 is a section taken in elevation on lines 7—7 of FIG. 6.

The sling has spaced apart, forwardly extending panels 10*a* and 10*b*, which are foldable to be connected together along upper extent 10*c* of the sling, as for example is shown in FIG. 7. Panel 10*a* is an inner panel positioned to rest against the user's side 14; and panel 10*b* is an outer panel positioned to extend as shown, adjacent the user's arm 12*b* in space 15. A connection is shown at 16 for interconnecting upper extents of the panels, in a forward and rearward direction 17. That connection may for example comprise hook and pile elements, as shown, enabling ready release of the connection 16.

Figure 5:
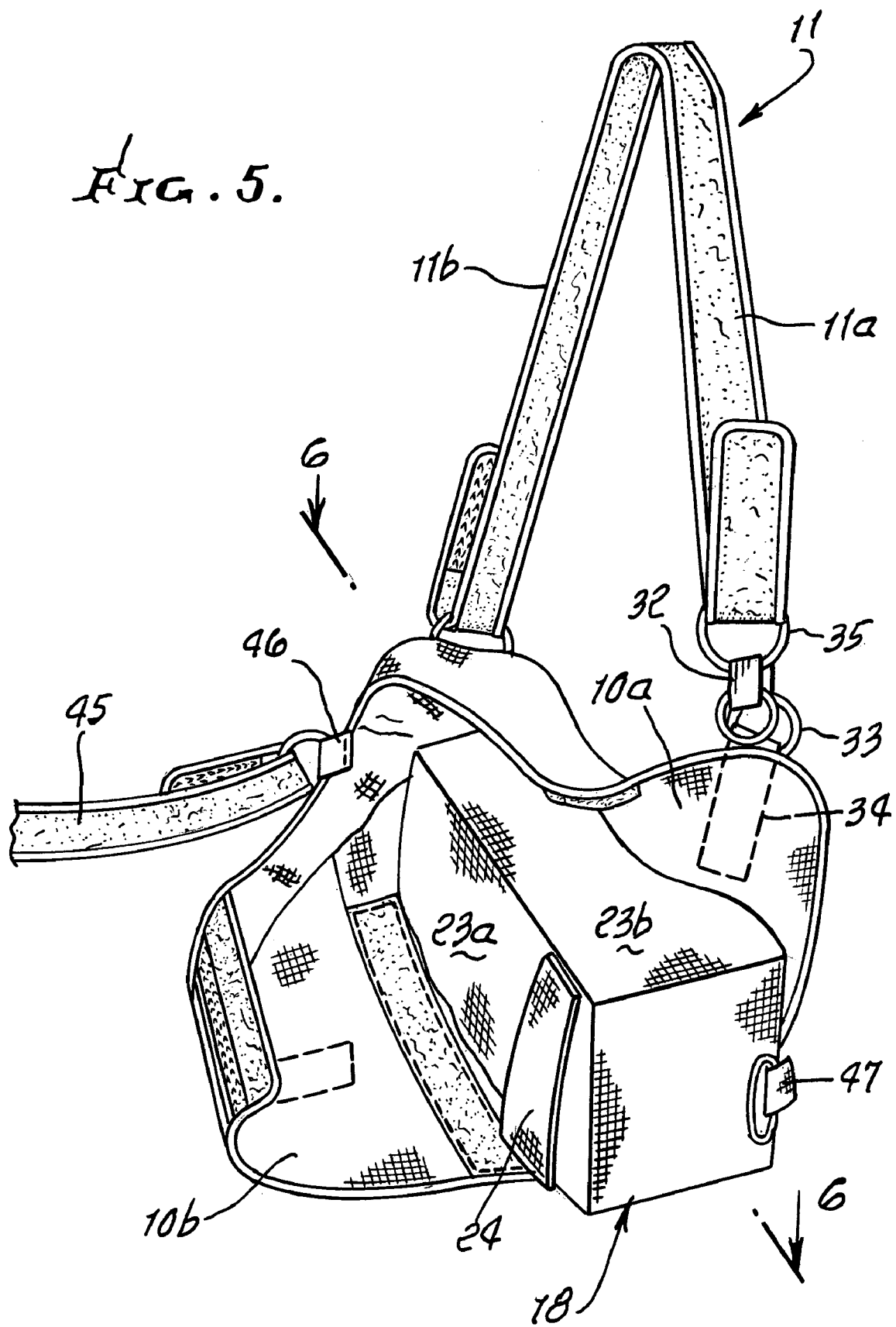
FIG. 5 is a more detailed view, taken in frontal perspective, showing the opened sling, and pillow.
Figure 6:
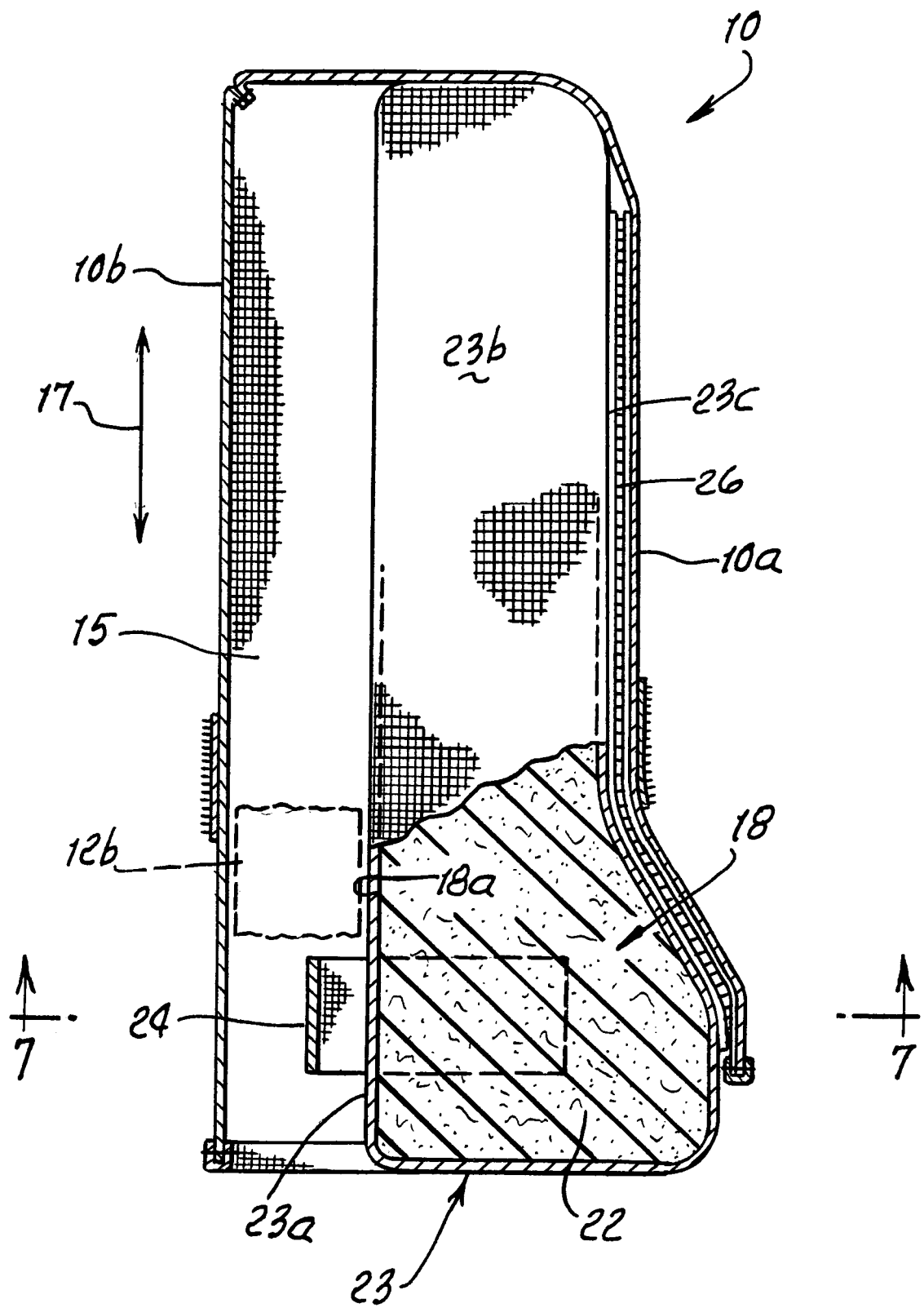
FIG. 6 is a plan view taken in section on lines 6—6 of FIG. 5.

An insert pillow 18 is received into the sling, as for example downwardly when connection 16 is opened as seen in FIG. 5. The received pillow is located in space 20, between arm space 15 and panel 10*a*, whereby the pillow comfortably holds the user's arm 12*b* in outwardly spaced relation to the user's side 14, the tensioned sling panel 10*b* holding the user's arm against the pillow side 18*a*. The pillow may consist of yieldably compressible pad material 22 such as foam rubber, or foam plastic, and a jacket 23 surrounding the pad, as at 23*a*–23*d*, in FIG. 7. A finger or hand retention strap 24 extends adjacent the forward end of the pillow at its side facing space 15. The strap lower end 24*a* has hook and loop connection to the pillow, bottom panel 10*e* as at 70.

The pillow itself preferably has adjustable VELCRO connection to the sling, as at connection 26 to sling panel 10*a*, to adjustably position the pillow in the sling, for most comfort to the user's arm 12*b*.

Sling strap 11*a* has connection to upper portions 10*a*' and 10*b*' of both sling panels 10*a* and 10*b*, as seen in FIG. 7. See ring 30 connecting adjustable strap 32 to loop 32*a*; and see ring 33 connecting adjustable strap 32*b* to loop 32. Ring 35 connects loop 32 to sling shoulder strap 11*a*, as shown. Hook and loop connections 31*a* and 34*a* allow length adjustment of folded-back straps 31 and 34 whereby rotary positioning (see arrow 50) of the pillow in the sling can be achieved; and hook and loop connection 37 allows length adjustment of sling strap 11*b*.

Figure 2:
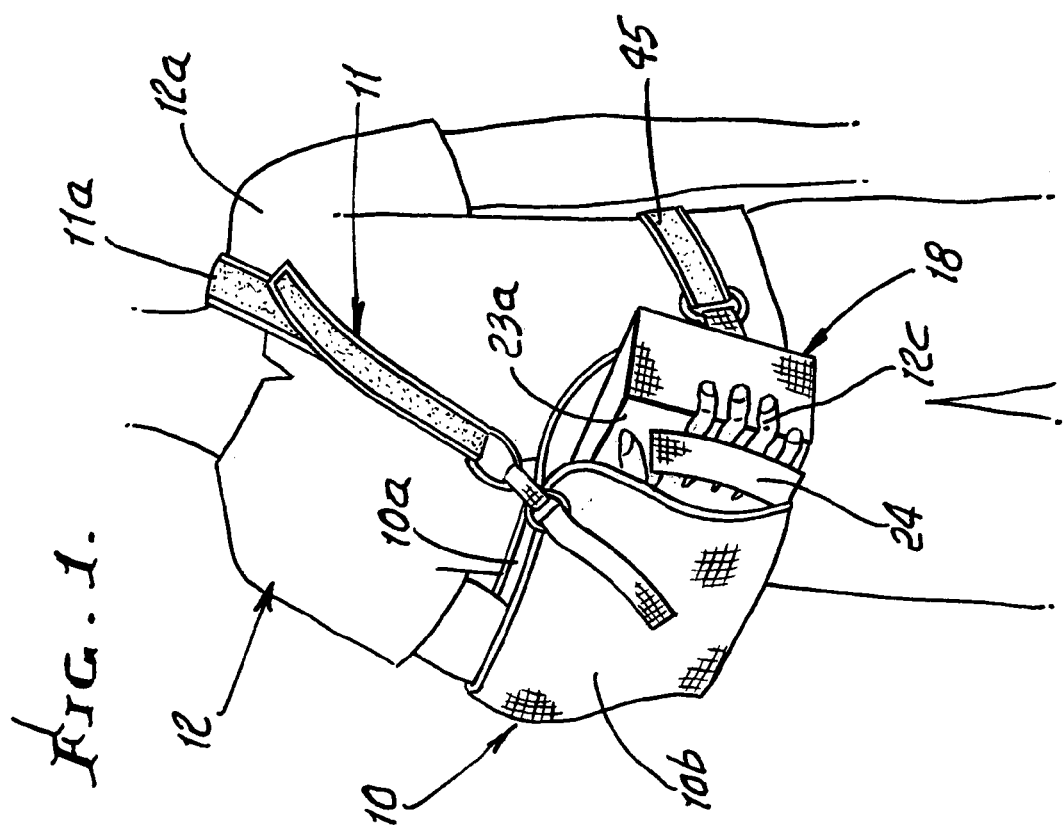
Figure 3:
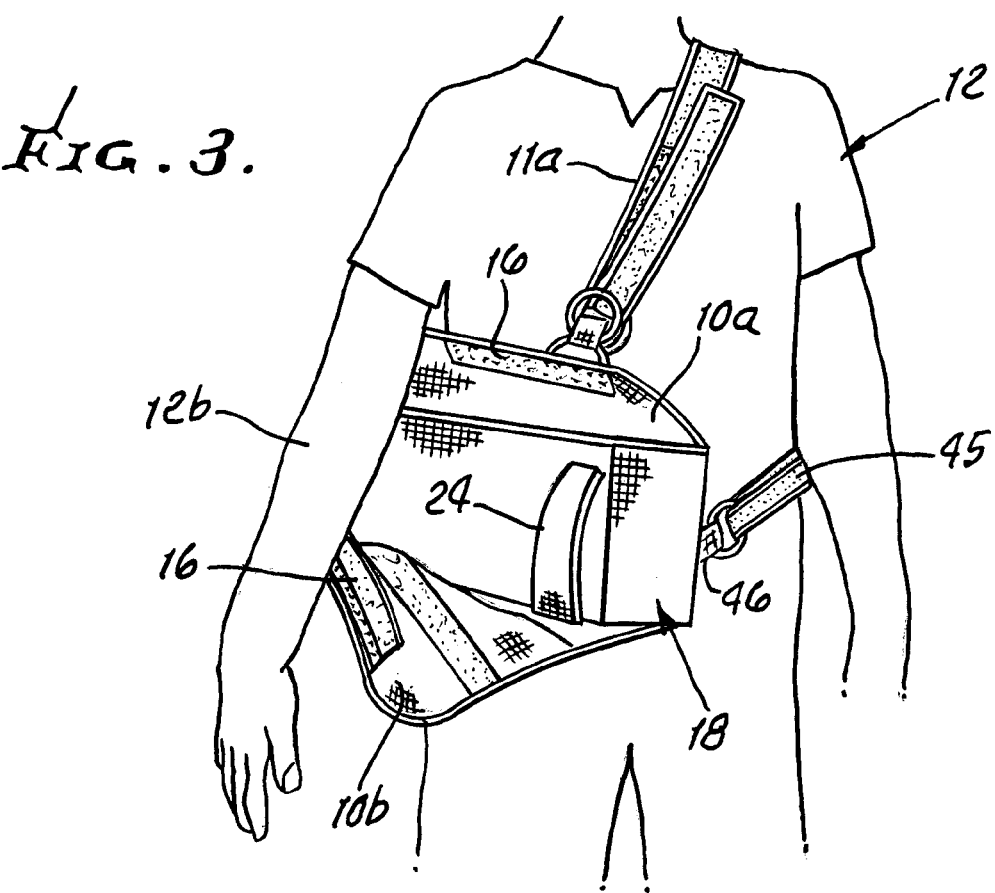
FIG. 3 is a view showing sling panels separated away from a pillow retained in the sling.
Figure 4:
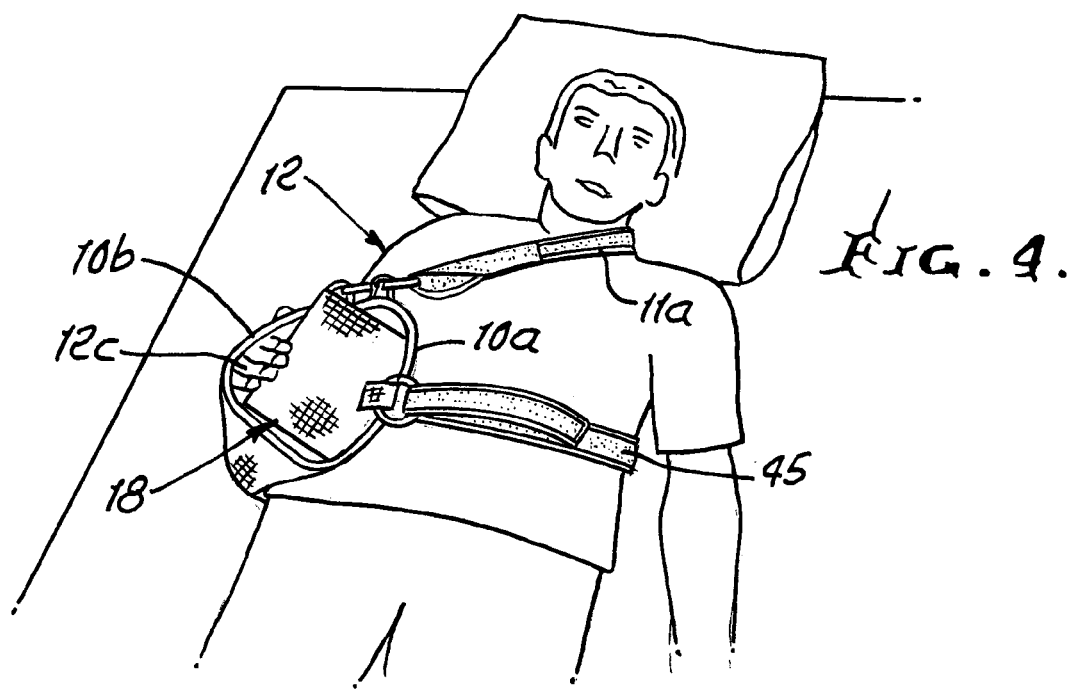
FIG. 4 is a view of a bedridden patient to which the sling apparatus and pillow are easily applied, as for example by pillow insertion into the opened sling.

When strap 31 is disconnected from panel 10*b*, outer sling panel 10*b* can be dropped, after release of the connection 16. This allows alternative downward flexing and positioning of the user's arm 12*b*, as to a hanging condition, as seen in FIG. 3, below the level of the sling panel 10*b*, as for arm medical or other treatment, without requiring removal of the pillow 18 from the sling. Thereafter, the user's forearm 12*b* can be flexed up at the elbow and re-positioned adjacent the pillow side as in FIG. 7, and the panel 10*b* re-attached at 16 to panel 10*a*, and strap 31 re-attached to loop 32. These steps can be easily accomplished while the user is in lying or reclining position, as in a medical facility as seen in FIG. 4, without disturbing the sling straps 10*a* and 10, or a body retention strap 45. The latter has attachment to the sling at 46, as seen in FIG. 2, and to the pillow at 47 as seen in FIG. 5. These connections assure positioning of the pillow in the sling, during use and adjustment. The user's hand 12*c* is shown in FIG. 1, retained to the pillow by strap 24.

Figure 8:
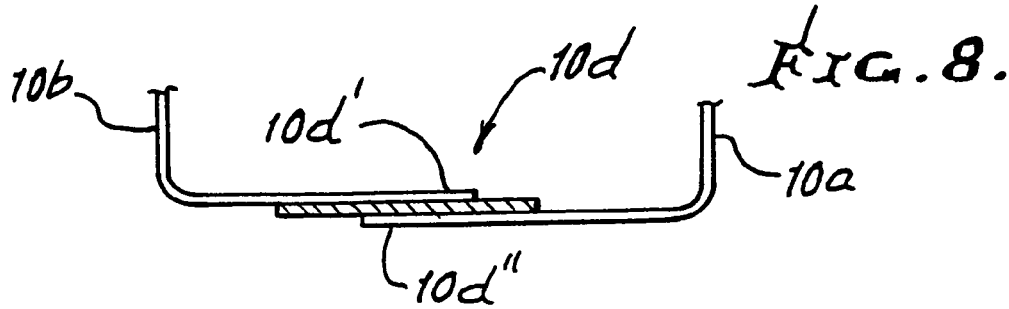
FIG. 8 is a vertical section showing a modification.

FIG. 8 shows an optional sling bottom panel 10*d* which is adjustable in width between side panels 10*a* and 10*b*. See overlapping sections 10*d'* and 10*d"* of panel 10*d*, VELCRO connected to allow width adjustment of 10*d*, below the pillow.

The pillow width is typically between 2½ and 6 inches. The pillow may consist of an inflatable container, rather than foam rubber of foam plastic.

I claim:

1. An arm supporting pillow in sling apparatus, comprising in combination
   a) a flexible sling, with a strap to be supported by a user's shoulder area,
   b) an insert pillow received in the sling, and retrievable from the sling, the pillow having elongated block shape, and the sling and inner side of the pillow each having adjustable hook and loop configurations adapted for attachment of the pillow to the inner side of the sling,
   c) the sling and pillow dimensioned to receive a user's forearm alongside the pillow, in the sling,
   d) the sling having forwardly extending panels which are foldable to be connectable together along upper extent of the sling, spaced above the pillow, to close the sling over the user's forearm and pillow, and to allow upward opening of the sling to release the user's forearm and the pillow,
   e) there being a user's forearm receiving pocket formed between the pillow in the sling and outer extent of the sling facing inwardly toward the pillow, and defining one of said panels.

2. The combination of claim 1 wherein the pillow has a width between 2½ inch and 6 inches.

3. The combination of claim 1 wherein the strap has releasable connection to the sling, proximate fore and aft ends thereof.

4. The combination of claim 1 wherein the sling has a releasable drop panel which, when dropped, allows the user's forearm to dangle downwardly from and below the sling.

5. The combination of claim 4 wherein the drop panel, when released, dangles downwardly from a rear portion of the sling while remaining carried by the sling.

6. The combination of claim 1 including a hand holder carried adjacent a fore portion of the pillow.

7. The combination of claim 6 wherein the hand holder comprises a strap, adjustably attached to the pillow.

8. The combination of claim 1 wherein the pillow consists of foam material, and has a jacket covering the foam material.

9. The combination of claim 8 wherein said pillow consists of one of the following:
   i) foam rubber,
   ii) foam plastic,
   iii) an inflatable container.

10. The combination of claim 1 including a body strap having opposite ends respectively connected to the sling and to the pillow, and having length to extend about the user's body.

11. The combination of claim 1 wherein the pillow has releasable connection to the sling.

12. The combination of claim 1 wherein the pillow has releasable connection to one of the panels.

13. The combination of claim 1 including the sling having a bottom panel which is adjustable in width to allow sling size adjustment.

14. The combination of claim 1 wherein the sling strap has adjustable connection to said panels, allowing limited rotary adjustment of the sling and pillow about a forwardly extending axis.

* * * * *